United States Patent
Haraldsson et al.

(10) Patent No.: US 9,005,580 B2
(45) Date of Patent: Apr. 14, 2015

(54) TREATMENT OF RENAL CELL CARCINOMA

(75) Inventors: Borje Haraldsson, Lanvetter (SE); Ulf Nilsson, Goteborg (SE); Lisa Buvall, Brookline, MA (US); Jenny Nystrom, Hovas (SE)

(73) Assignee: Oncorena AB, Gothenburg (SE)

( * ) Notice: Subject to any disclaimer, the term of this patent is extended or adjusted under 35 U.S.C. 154(b) by 68 days.

(21) Appl. No.: 13/638,888

(22) PCT Filed: Mar. 28, 2011

(86) PCT No.: PCT/SE2011/050341
§ 371 (c)(1),
(2), (4) Date: Dec. 14, 2012

(87) PCT Pub. No.: WO2011/123027
PCT Pub. Date: Oct. 6, 2011

(65) Prior Publication Data
US 2013/0101507 A1   Apr. 25, 2013

Related U.S. Application Data

(60) Provisional application No. 61/341,577, filed on Apr. 1, 2010.

(51) Int. Cl.
| | | |
|---|---|---|
| A61K 51/04 | (2006.01) | |
| A61K 31/444 | (2006.01) | |
| A61K 35/74 | (2006.01) | |
| A61K 39/00 | (2006.01) | |
| A61K 45/06 | (2006.01) | |
| A61K 47/48 | (2006.01) | |
| A61K 51/06 | (2006.01) | |
| A61K 51/08 | (2006.01) | |
| A61K 31/765 | (2006.01) | |

(52) U.S. Cl.
CPC .......... *A61K 51/0497* (2013.01); *A61K 31/444* (2013.01); *A61K 35/74* (2013.01); *A61K 39/00* (2013.01); *A61K 45/06* (2013.01); *A61K 47/48215* (2013.01); *A61K 47/4823* (2013.01); *A61K 51/065* (2013.01); *A61K 51/08* (2013.01); *A61K 31/765* (2013.01)

(58) Field of Classification Search
CPC .......................... A61K 51/0497; A61K 51/065
USPC .......................... 424/1.85, 1.89; 514/183, 334
See application file for complete search history.

(56) References Cited

U.S. PATENT DOCUMENTS

2010/0152243 A1   6/2010   Haraldsson et al.

FOREIGN PATENT DOCUMENTS

| WO | WO-9500117 | * | 1/1995 |
| WO | WO 2010/040750 A1 | | 4/2010 |

OTHER PUBLICATIONS

Ji-Kai-Liu, N-Containing Compounds of Macromycetes, Chemical Reviews, vol. 105(7), 2723-2742, 2004.*
Danel V.C. et al., "Main features of *Cortinarius* spp. poisoning: a literature review", *Toxicon* 39,1053-1060 (2001).
International Search Report and Written Opinion Corresponding to International Application No. PCT/SE2011/050341; Date of Mailing: Jul. 19, 2011; 12 Pages.
Prast H. et al., "Toxic properties of the mushroom *Cortinarius orellanus* (Fries) II. Impairment of renal function in rats", *Arch Toxicol* 62,89-96 (1988).

* cited by examiner

*Primary Examiner* — Michael G Hartley
*Assistant Examiner* — Jagadishwar Samala
(74) *Attorney, Agent, or Firm* — Myers Bigel Sibley & Sajovec, P.A.

(57) ABSTRACT

Methods for treating renal cancer by administration of certain 3,3',4,4'-tetrahydroxy-2,2'-bipyridine-N,N'-dioxide compounds, especially 3,3',4,4'-tetrahydroxy-2,2'-bipyridine-N,N'-dioxide (Orellanine), conjugated to an alpha-emitting radionuclide (e.g. Astatine-211) to increase the efficacy of the formulation and/or a large molecule (e.g. a oligomer/polymer such as a PEG or a polysaccharide such as a dextran or a Ficoll®) to reduce the filtration and consequently the renal exposure. Particular administration protocols and dosing regimens, as well as pharmaceutical compositions suitable for use in the treatment methods can be used.

16 Claims, No Drawings

TREATMENT OF RENAL CELL CARCINOMA

STATEMENT OF PRIORITY

This application is a 35 U.S.C. §371 national phase application of International Application Serial No. PCT/SE2011/050341, filed Mar. 28, 2011, which claims the benefit, under 35 U.S.C. §119 (e), of U.S. Provisional Application Ser. No. 61/341,577, filed Apr. 1, 2010, the entire contents of which are incorporated by reference herein in their entireties.

TECHNICAL FIELD

The present invention relates generally to cancer treatment. More specifically this invention relates to the use of 3,3',4,4'-tetrahydroxy-2,2'-bipyridine-N,N'-dioxides, especially 3,3',4,4'-tetrahydroxy-2,2'-bipyridine-N,N'-dioxide (Orellanine), conjugated with an α-emitting radionuclide (e.g. Astatine 211) or a macromolecule (e.g. a PEG, a dextran or a FICOLL®) for the treatment of renal cancer, particularly renal cell carcinoma originating from renal proximal tubular cells.

BACKGROUND

Cancer appears in more than 100 different forms that affect nearly every part of the body. Throughout life, healthy cells in the body divide, grow, and replace themselves in a controlled fashion. Cancer results when the genes dictating this cellular division malfunction and cells begin to multiply and grow out of control. A mass or clump of these abnormal cells is called a tumor. Not all tumors are cancerous. Benign tumors, such as moles, stop growing and do not spread to other parts of the body. Cancerous or malignant tumors, however, continue to grow and smother healthy cells, interfere with body functions, and draw nutrients away from body tissues. Malignant tumors can spread to other parts of the body through a process called metastasis. Cells from the "mother tumor" detach, migrate via the blood or lymphatic vessels or within the chest, abdomen or pelvis, depending on the tumor, and they eventually form new tumors elsewhere in the body.

Cancer in the kidney constitutes about 3% of all solid tumors. About 85% of renal tumors are classified as renal cell carcinoma (RCC) Approximately 80% of diagnosed RCC originate from the epithelial cells lining the proximal parts of the kidneys' urine-forming ducts, the tubuli. Due to its appearance under the microscope, this cancer type is known as either renal clear cell carcinoma (RCCC, 65%) or renal papillary cell carcinoma (RPCC, 15%). While RCCC and RPCC constitute 80% of diagnosed RCC, they are responsible for closer to 100% of the deaths from renal cell carcinoma.

The most important factor in predicting prognosis is the stage. The stage describes the cancer's size and how deeply it has spread beyond the kidney. The Staging System of the American Joint Committee on Cancer (AJCC) is known as the TNM system. The letter T followed by a number from 1 to 3 describes the tumor's size and spread to nearby tissues. Higher T numbers indicate a larger tumor and/or more extensive spread to tissues near the kidney. The letter N followed by a number from 0 to 2 indicates whether the cancer has spread to lymph nodes near the kidney and, if so, how many are affected. The letter M followed by a 0 or 1 indicates whether or not the cancer has spread to distant organs.

Stage I: The tumor is 7 cm (about 2¾ inches) or smaller, and limited to the kidney. There is no spread to lymph nodes or distant organs.

Stage II: The tumor is larger than 7.0 cm but still limited to the kidney. There is no spread to lymph nodes or distant organs.

Stage III: Includes tumors of any size, with or without spread to fatty tissue around the kidney, with or without spread into the large veins leading from the kidney to the heart, with spread to one nearby lymph node, but without spread to distant lymph nodes or other organs. Stage III also includes tumors with spread to fatty tissue around the kidney and/or spread into the large veins leading from the kidney to the heart, that have not spread to any lymph nodes or other organs.

Stage IV: This stage includes any cancers that have spread directly through the fatty tissue and the fascia ligament-like tissue that surrounds the kidney. Stage IV also includes any cancer that has spread to more than one lymph node near the kidney, to any lymph node not near the kidney, or to any other organs such as the lungs, bone, or brain.

Detailed definitions of renal cell cancer, T, N, M categories, and stage groupings: Primary tumor (T):
TX: Primary tumor cannot be assessed
T0: No evidence of primary tumor
T1: Tumor 7 cm or less, limited to kidney
T2: Tumor greater than 7 cm, limited to kidney
T3: Tumor extends into major veins/adrenal/perinephric tissue; not beyond Gerota's fascia
T3a: Tumor invades adrenal/perinephric fat
T3b: Tumor extends into renal vein(s) or vena cava below diaphragm
T3c: Tumor extends into vena cava above diaphragm
T4: Tumor invades beyond Gerota's fascia
N—Regional lymph nodes
NX: Regional nodes cannot be assessed
N0: No regional lymph node metastasis
N1: Metastasis in a single regional lymph node
N2: Metastasis in more than one regional lymph node
M—Distant metastasis
MX: Distant metastasis cannot be assessed
M0: No distant metastasis
M1: Distant metastasis As a rule of thumb, cancer in stages I or II is treated by surgical removal of the afflicted kidney and the prognosis for recovery is good. Approximately 95% of all RCC are unilateral, meaning that the vast majority of all RCC patients are left with one remaining, healthy kidney after treatment. One functional kidney is generally considered more than enough for adequate glomerular filtration and general kidney function, meaning that patients with unilateral RCC in stages I or II are likely to live a perfectly normal life after treatment. For the remaining 5% of the patients, suffering from bilateral RCC, treatment often involves removal of both kidneys. This leaves the patient dependent on renal dialysis (hemodialysis or peritoneal dialysis) for life or until a renal transplant can be scheduled. If the tumors are small and well defined, kidney-conserving surgical techniques, involving partial removal of one or both kidneys, may leave bilateral RCC patients with sufficient remaining tissue to uphold normal or partial renal function. The benefits of these techniques (i.e. remaining renal function) must be weighed against the potential reoccurrence of RCC if even a microscopic part of the tumor escapes excision.

In contrast to the above, renal cancers of stage III or IV are associated with very low survival rates, and the National Cancer Institute states on its website that "Virtually no patients with renal cell cancer in stage IV can be cured."

The National Cancer Institute estimates 49,096 new cases of renal cancer to have been diagnosed in the U.S. in 2009 ($16/10^5$ citizens) with 11,033 ensuing deaths ($3.6/10^5$ citizens). The corresponding numbers for the European Union (2006) are 65,051 diagnoses ($7.8/10^5$ citizens) and 27,326 deaths ($3.3/10^5$ citizens) (*European Cancer Observatory*: Estimated incidence and mortality 2006). Worldwide estimates (2006) are 209,000 diagnosed cases ($3.2/10^5$ citizens) and 102,000 deaths ($1.6/10^5$ citizens) (Gupta et al. Cancer Treat. Rev. 34, 193-205; 2008). The seemingly higher incidence in the U.S. is due to the fact that the NCI co-reports cancer of the renal pelvis (which is relatively easy to treat) with renal cell carcinomas. The lower global incidence and death rates are likely due, at least in part, to under diagnosis in large areas of the Third World.

The main problem with conventional art is that, as mentioned above, the outcome for any one patient diagnosed with renal cancer is dictated largely by the timing of the diagnosis. If the disease is diagnosed before the tumor has spread outside the kidney the chance for survival is good, otherwise most patients die from the disease. The main reason for this is that renal cell carcinoma is refractory to all conventional therapy with cytostatic and/or cytotoxic drugs, such as cisplatin, carboplatin, docetaxel, paclitaxel, flurouracil, capecitabine, gemcitabine, irinotecan, topotecan, etoposide, mitomycin, gefitinib, vincristine, vinblastine, doxorubicin, cyclophosphamide, celecoxib, rofecoxib, and/or valdecoxib.

Various solutions are described in the prior art. Conventional chemotherapy against renal cell carcinoma is generally contraindicated due to poor effectiveness and extensive side effects. Alternative treatment modalities have thus been sought, and they can be divided into several categories:
1) Antiangiogenesis. In this strategy the tumor is denied nutrients and oxygen through inhibition of formation of the blood vessels necessary for supplying the tumor tissue. This can be achieved in several ways: 1a) inhibition of circulating growth factors, such as VEGF, PDGF, and PlGF, by treatment with antibodies directed against these growth factors; 1b) blocking of receptors for vascular growth factors on target cells with antibodies directed against the receptors; and 1c) treatment with smaller molecules that interfere with receptor function in such a way that binding of a vascular growth factor to its receptor fails to elicit the physiological angiogenetic effect.
2) Immunomodulatory treatment. This strategy attempts to stimulate the endogenous immune system to recognize the tumor cells as alien and start fighting them. Immune stimulation as treatment against renal cancer takes two main routes: 2a) treatment with interleukin 2 (IL-2); and 2b) interferon alpha (IFN-α) therapy.

All of the alternative treatment strategies mentioned above significantly improve the life span of some patients with renal cancer in an advanced stage. However, the effect is in the order of only a few months, and the treatment is associated with numerous serious side effects. Very often the tumor adapts to the treatment, which then has to be discontinued. This is followed by an accelerated rate of tumor growth.

Recent strategies for the treatment of renal cancer have been reviewed by Garcia et al., ("Recent progress in the management of advanced renal cell carcinoma." *CA Cancer. J. Clin.* 57(2): 112-25 (2007)) and by Atkins et al. ("Innovations and challenges in renal cell carcinoma: summary statement from the Second Cambridge Conference." *Clin. Cancer. Res.* 13(2 Pt 2): 667s-670s (2007)). A review of the literature indicated that many of the therapeutic approaches originate from the identification of more or less specific cancer markers and the use of these markers to elicit a host immune response directed against the invading tumor tissue. See for example, US2006134708 disclosing several molecular markers of kidney and urothelial cancer, namely IGFBP-3 (insulin-like growth factor-binding protein 3), ANGPTL4 (angiopoietin-like 4) and ceruloplasmin, as well as monoclonal antibodies directed against said markers, for diagnostic purposes.

U.S. Pat. No. 6,440,663 teaching different genes expressed by renal cancer cells and US 2005261178 teaching the co-administration of a monoclonal antibody (G250), directed against an antigen (carbonic anhydrase IX) expressed on the majority of renal cancers, and the cytokines Interleukin-2 or Interferon-α are other examples of such approaches.

Other strategies are based on the use of known therapeutic substances in new treatment regimes. For example, US20090131536 discloses the use of previously known dimethane sulfonate compounds, in particular NSC-281612, according to a new administration protocol in order to treat renal cancer. When tested on xenografts in nude mice, administration of NSC-281612 led, in some cases, to apparently complete eradication of the tumor mass.

Finally, in a few instances, suggested therapy is founded on new original substances. Thus, US20060025484 discloses the use of 1-(2-chloroethyl)-1-nitroso-3-(2-hydroxyethyl) urea (HECNU) for the treatment of many cancer types, including renal cancer. The main feature of HECNU is an improved water solubility compared to the previously known corresponding compound, Bis-(2-chlorethyl)-1-nitroso-urea (BCNU).

EP1712234 discloses the use of 4-pyridylmethyl-phthalazine derivatives as VEGF receptor inhibitors in the treatment of renal cancer, especially for the inhibition of metastatic growth. It was found that co-administration of the 4-pyridyl-methyl-phthalazine derivatives with either of a plurality of conventional chemotherapeutic agents had a synergistic effect, even though the tumor cells are refractory to the chemotherapy alone. Further, combination therapy was associated with noticeably smaller side effects.

The invention herein is based on Orellanine (Formula I), which is a selective renal toxin occurring in relatively large amounts in several fungal species of the *Cortinarius* family. Intoxication with Orellanine after confusion of *Cortinarius* fungi with edible mushrooms occurs regularly throughout Europe, Russia and North America. After ingestion of Orellanine-containing fungi, there is a period of a few days up to 3 weeks with no symptoms or only mild, influenza-like symptoms. The next phase, when medical help is generally sought, is characterized by uremia due to acute renal failure. Despite many descriptions of Orellanine poisoning in the scientific literature, no other effects of Orellanine have been reported apart from the renal toxicity just mentioned (Danel V C, Saviuc P F, Garon D: Main features of *Cortinarius* spp. poisoning: a literature review. Toxicon 39, 1053-1060 (2001).). This selectivity most likely resides with the fact that Orellanine is taken up specifically by one cell type, i.e., the tubular epithelial cells, particularly the proximal tubular epithelial cells (Prast H, Pfaller W: Toxic properties of the mushroom *Cortinarius orellanus* (Fries) II. Impairment of renal function in rats. Arch Toxicol 62, 89-96 (1988)). The toxin mechanism of Orellanine has not been elucidated, and no treatment is available except maintenance dialysis while waiting to see whether the kidneys will recover or not. The final outcome is critically dependent on the amount of toxin ingested, and, as a rule of thumb, ingestion of one fungus gives temporary problems, two fungi leads to permanent loss of part of the renal function whereas three or more fungi results in total loss of renal function and lifelong need for renal replacement therapy in the form of dialysis or kidney transplantation.

The applicants have recently published a first study of the mode of action of Orellanine in healthy rats (Nilsson U A et al. The fungal nephrotoxin orellanine simultaneously increases oxidative stress and down-regulates cellular defenses. Free Rad. Biol. Med. 44:1562-9 (2008).). This study shows increased oxidative stress in cortical renal tissue along with dramatically decreased expression of several key antioxidant genes. During this work it was realized that the specificity of Orellanine for renal tubular epithelial cells, which is in prior art generally considered to be absolute, could theoretically be extended to encompass these cells also after their transformation into cancer cells. If proven true, such a hypothesis would mean that Orellanine is a powerful weapon against renal cancer of epithelial origin, with curative potential even in advanced stages and with metastases in other tissues.

Pursuing this hypothesis, it was surprisingly discovered that Orellanine is indeed taken up also in human renal cancer cells, and kills them with great efficiency whether they are derived from a primary tumor or from metastatic tumor tissue. The cell death progresses for many days after transient exposure to Orellanine, indicating that the toxin is actively taken up and retained by the cells (see co-pending application US2010-0152243).

Although the discovery that Orellanine can target and kill renal cancer cells tremendously improved our ability to cure RCC in advanced stages, two significant drawbacks of the treatment are obvious:

Due to the target profile of Orellanine, treatment will inevitably lead to destruction of healthy renal tissue along with eradication of the metastatic tumor(s). This results in total renal failure, creating a need for life-long hemodialysis/peritoneal dialysis or kidney replacement by transplantation.

The notion of the high degree of specificity for Orellanine for normal (and transformed) renal tubular epithelial cells stems largely from intoxication data. In these cases a single dose of toxin was ingested in the form of mushrooms, and the vast majority of Orellanine in the ingested material was shunted to the kidneys simply by virtue of the extreme perfusion of these organs, receiving 20% of cardiac output. This means that Orellanine was rapidly filtered through the kidneys, and what was not taken up and retained by the tubular cells was lost in the urine. Consequently, the rest of the body was not exposed to significant concentrations of Orellanine. At least some of the observed specificity of Orellanine likely stems from this fact. Actually, the very fact that the toxin was taken up in to the bodies of those intoxicated clearly demonstrates that the specificity is not absolute; Orellanine must have been taken up and excreted into the blood by the epithelial cells lining the intestine. The setting during treatment for RCC is quite different: The overwhelming majority of the initial dose is eliminated through the kidneys, leading to the destruction of tubular cells and shutdown of remaining renal function. Subsequent doses, however, result in dramatically higher plasma concentration of Orellanine. This allows active uptake into the tumor cells of tubular origin, and these cells act, to some extent, as a sink that prevents exposure of other tissues to Orellanine. Nevertheless, spillover into other cell types is likely if high enough doses are used (as may be necessary to achieve total eradication of the tumor(s)). Thus, in spite of the apparent specificity of Orellanine, there may be collateral damage to other tissues when using it for treatment of RCC. This requires careful titration of the dose and regimen to balance the desired and undesired effects.

Accordingly there is a need for products and methods aimed to reduce the unwanted toxic effects of Orellanine in order to spare healthy renal tubular epithelial cells (and consequently renal function) as well as other cells that can be damaged by unspecific Orellanine toxicity. The present invention satisfies this need and provides further advantages as well.

SUMMARY

A primary object of the present invention is to provide a method for treating renal cancer originating from epithelial cells, which method involves administering to a mammal in need thereof at least one compound according to Formula I, comprising at least one α-emitting radionuclide (e.g. Astatine-211 or Actinium-225) attached at any of positions R1-R4.

Formula I

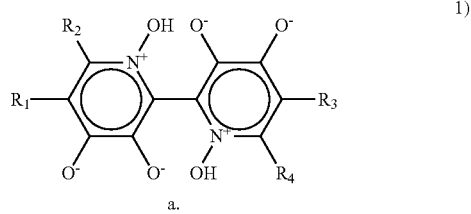

a.

Another object of the present invention is to provide a method for treating renal cancer originating from epithelial cells, which method involves administering to a mammal in need thereof at least one compound according to Formula I, comprising at least one α-emitting radionuclide (e.g. Astatine-211 or Actinium-225) attached at any of positions R1-R4, said compound being conjugated to at least one macromolecule (e.g. a oligomer/polymer such as a polyethylene glycol (PEG), a dextran or a FICOLL®) attached to any of positions R1-R4, said macromolecule having a molecular weight or diameter sufficient to substantially reduce or prevent glomerular filtration of said conjugate, wherein the alpha-emitting radionuclide and the macromolecule are preferably conjugated to different pyridyl moieties in the Orellanine molecule.

Another object of the present invention is to provide a method for treating renal cancer originating from epithelial cells, which method involves administering to a mammal in need thereof at least one compound according to Formula I, conjugated to at least one macromolecule (e.g. a oligomer/polymer such as a polyethylene glycol (PEG), a dextran or a FICOLL®) attached to any of positions R1-R4, said macromolecule having a molecular weight or diameter sufficient to substantially reduce or prevent glomerular filtration of said conjugate.

Other objects of the present invention are to provide a compound according to Formula I, conjugated with an α-emitting radionuclide or a macromolecule, for use as a medicament, and to provide a compound with conjugated Formula I for use in the treatment of renal cell carcinoma.

Other objects of the present invention are to provide a compound according to Formula I, conjugated with both an α-emitting radionuclide and a macromolecule, for use as a medicament, and to provide a compound with conjugated Formula I for use in the treatment of renal cell carcinoma.

Another object of the present invention is to provide a pharmaceutical composition comprising at least one compound according to any of the above conjugated forms of Formula I, optionally comprising other agents with anti-cancer activity, as well as carriers and any other excipients needed to optimize the effectiveness of the composition.

Yet another object is to provide a kit that contains the above composition, in one or more separate compartments, along with diluents and/or solvents and/or reagents for on-site coupling of alpha-emitter to the Orellanine molecule as needed, such that the composition easily can be made ready for use by the treating physician or nurse and/or a skilled technician in the area of therapy involving radionuclides.

Upon reading of the description and the examples, other objects and advantages of the present invention will become obvious to the person with normal skills in this field, and these objects and advantages are intended to fall within the scope of the present invention.

DETAILED DESCRIPTION AND PREFERRED EMBODIMENTS

The present invention provides pharmaceutical compositions comprising pyridine-N-oxide and bipyridine-N,N-dioxide compounds, conjugated with an α-emitting radionuclide (e.g. Astatine 211) and/or a macromolecule (e.g. PEG), and methods of treating renal cancer by administering the pharmaceutical compositions to a patient suffering from or susceptible to renal cancer. The invention herein also includes a kit for treating a patient suffering from or susceptible to renal cancer.

The present invention is a modification of Orellanine, and related compounds according to Formula I, for reducing the unwanted toxic effects of Orellanine and in order to spare healthy renal tubular epithelial cells as well as other cells that can be damaged by unspecific Orellanine toxicity. Thus, we provide products and methods according to the following embodiments:

A: The first embodiment of the present invention is based on a conjugation between compounds of Formula I and a macromolecule with a molecular weight sufficiently high to substantially reduce or prevent renal filtration of the conjugate. Thus, exposure of the proximal tubular cells to the toxin, which is actively taken up into the cells from primary urine, is significantly reduced. Basically the combination alters the pharmacokinetic properties of the formulation. The macromolecule could be e.g. an oligomer/polymer such as PEG, a polysaccharide such as a FICOLL® or a dextran.

PEG is an oligomer or polymer of ethylene oxide. PEG is commercially available over a very broad range of molecular weights (from 300 g/mol to 10,000,000 g/mol) and with different geometries (e.g. branched, linear and different combinations thereof). PEG has been conjugated to various proteins and peptides in order to obtain a more favorable pharmacokinetic profile. For example, patents such as WO08054585A, P2001288110 and U.S. Pat. No. 7,683,030B disclose conjugation of PEG to different drugs for increasing circulating half-life, decreasing the smallest therapeutically effective dose and reducing kidney clearance of the modified drug molecules. Albeit less common in the prior art, small molecules can also be conjugated with PEG. (Bersani et al, (2005) Farmaco 60(9):783-8).

Dextran, a complex, branched glucan composed of chains of varying lengths (generally from 10 to 150 kD) and FICOLL®, a neutral, highly branched, high mass hydrophilic polysaccharide are examples of other substances also commonly use to prolong the effect of pharmaceuticals.

We have utilized the properties of different macromolecules (including, but not limited to, PEG, dextran and FICOLL®), in combination with the high degree of specificity for Orellanine in normal and transformed renal tubular epithelial cells, to create conjugated molecules that both stay longer in the blood and display surprisingly low toxicity towards healthy renal cells. To our knowledge, this type of conjugation has not previously been used to create a drug that selectively targets metastatic cancer cells, originating from renal tubular epithelial cells, while sparing healthy tubular cells in unaffected renal tissue.

As explained above, the nature of the conjugating macromolecule is such that it does not substantially interfere with toxicity, specificity and uptake of the Orellanine moiety of the conjugate into renal cancer cells. Conjugating a compound of Formula I to a macromolecule of sufficient size retains the conjugate in the circulatory system through lowered glomerular filtration, and renal exposure is thus markedly reduced. Healthy renal tubular epithelial cells can hence be spared (e.g. in the healthy kidney of a unilateral renal cancer). This embodiment of the present invention makes it possible to selectively treat metastatic renal cancer of tubular epithelial origin with sufficiently low exposure of healthy kidney tubular epithelial cells to the toxic compound to leave the patient with adequate kidney function after successful treatment. In this way dialysis therapy may be avoided, leading to greatly improved quality-of-life for the treated individual and substantially reduced strain on the health care-system since care of the typical dialysis patient costs ten times as much as that of the average patient.

Coupling of a macromolecule to a target compound according to Formula I can be carried out according to standard methods, with protection of sensitive substituents as needed, which are known to the normally skilled professional worker within the field of organic synthesis. These standard methods include covalent or noncovalent association of compounds according to Formula I of the invention with a macromolecule, such as an oligomer/polymer (e.g., a PEG, a polylysine, a dextran, etc.), a branched-chain polymer; a lipid; a cholesterol group (such as a steroid); or a carbohydrate, oligosaccharide or a polysaccharide (e.g. a FICOLL®). Other possible carriers include one or more water-soluble polymer attachments such as polyoxyethylene glycol, or polypropylene glycol as described e.g. in U.S. Pat. Nos. 4,640,835, 4,496,689, 4,301,144, 4,670,417, 4,791,192 and 4,179,337. Still other useful polymers known in the art include monomethoxy-PEG, cellulose, or other carbohydrate based polymers, poly-(N-vinyl pyrrolidone)-polyethylene glycol, propylene glycol homopolymers, a polypropylene oxide/ethylene oxide copolymer, polyoxyethylated polyols (e.g., glycerol) and polyvinyl alcohol, as well as mixtures of these types of macromolecules.

In one preferred embodiment of the invention, the carrier is a PEG. The PEG group may be of any convenient molecular weight and may be straight chain or branched. The average molecular weight of the PEG will range from about 2 kDa to about 100 kDa, or from about 5 kDa to about 50 kDa, or from about 5 kDa to about 10 kDa.

The PEG groups will generally be attached to the compounds of the invention via acylation, reductive alkylation, Michael addition, thiol alkylation or other chemoselective conjugation/ligation methods through a reactive group on the PEG moiety (e.g., an aldehyde, amino, amido ester, thiol, alpha-haloacetyl, maleimido or hydrazino group) to a reactive group on the target compound (e.g., an aldehyde, amino, amido, ester, thiol, alpha-haloacetyl, maleimido or hydrazino group).

B: The second embodiment of the present invention is based on a conjugation between compounds of Formula I and an α-emitting radionuclide (e.g. Astatine 211) to increase the treatment efficacy of the formulation by creating a species with a target profile and specificity similar to Orellanine but with vastly increased toxicity Thus, the dose of $^{211}$At-conjugated Orellanine required for efficient tumor eradication is low enough that no unspecific uptake into other tissues occurs, meaning that collateral toxicity is substantially or completely avoided.

For many years, beta-emitting radionuclides have been used as cytotoxic agents in radiopharmaceuticals for cancer therapy. Recently, however, efforts have also been made to utilize alpha-emitters in anti-tumor agents. Examples of alpha-emitters include nuclei of some unstable isotopes, such as Astatine 211, Bismuth-212, Bismuth-213, Actinium-225, Lead-212 and Terbium-149, which decay by emitting α-particles. Alpha-emitters have several features that distinguish them from beta-emitters and potentially provide for better effectiveness in therapy. These include higher energies and shorter ranges in tissues. The radiation range of typical alpha emitters in physiological surroundings is generally less than 100 micrometers, the equivalent of only a few cell diameters. This makes these sources well suited for treatment of tumors including micro-metastases because little of the radiated energy will pass beyond the target cells, minimizing damage to the surrounding healthy tissue. In contrast, a beta particle has a range of 1 mm or more in water. The energy of alpha-particle radiation is also high compared to beta particles, gamma rays and X-rays, typically being 5-8 MeV, or 5 to 10 times that of a beta particle and 20 or more times the energy of a gamma ray. Thus, this deposition of a large amount of energy over a very short distance gives alpha radiation an exceptionally high linear energy transfer (LET), compared to gamma or beta radiation. Under favorable conditions, a single alpha particle is sufficient to destroy a cancer cell. This explains the exceptional cytotoxicity of alpha-emitting radionuclides and also imposes stringent demands on the level of control and study of radionuclide distribution necessary in order to avoid unacceptable side effects.

There are several examples about the use of alpha-emitting radionuclides in cancer therapy. However the vast majority of published papers and patents concerning alpha-emitters in cancer radiotherapy, pertain to radio-immunotherapy (RIT), which takes advantage of the specificity of the antigen-antibody interaction by conjugating an alpha-emitter to an antibody raised against an antigen presented only or mainly on the cancer cells. In this way radionuclides that emanate lethal doses of cytotoxic radiation can be delivered to tumor cells while avoiding collateral damage to a degree that depends on how unique the antigen expression is to the cancer cells. Other uses relate to methods for minimizing side effects.

Astatine-211 has one distinct advantage over most other alpha-emitting nuclides used in therapy, namely its chemical character. Astatine is a halogen with a chemistry allowing covalent coupling to other molecules, including Orellanine, while other available nuclides are of metallic character and generally require chelating agents for conjugation. Furthermore, Astatine-211 is produced relatively easily by bombarding natural bismuth with alpha particles in a cyclotron. Nuclear reaction is followed by dry distillation of the bismuth target and collection of $^{211}$At in chloroform. (Zalutsky M R et. al.: J. Nucl. Med. (2001) 42:1508-15). Coupling of $^{211}$At to a carrier molecule can be carried out according to standard methods for halogenations, e.g. iodination, of organic molecules, with protection of sensitive substituents as needed, which are known to the normally skilled professional worker within the field of organic synthesis.

In the present invention by combining two different mechanisms of toxicity, i.e. the general cytotoxicity of e.g. Astatine 211 or Actinium-225 and the targeted toxicity of compounds of Formula I on renal tubular epithelial cells and cancer cells of tubular origin, we have generated a conjugated compound with surprisingly strong and specific effects on renal cancer cells. The nature of the attached radionuclide is such that it substantially increases the toxicity of the conjugate compared to unconjugated compound of Formula I, while not interfering substantially with specificity or uptake into renal cancer cells. This enables us to reach satisfactory treatment effects with strikingly low concentrations of Orellanine, approximately 10% of the most preferred dose of unconjugated compounds of Formula I, hereby substantially attenuating or eliminating the unspecific toxicity of Orellanine.

C: The third embodiment of the invention is a combination of the first (A) and second embodiments (B), conjugating a compound according to Formula I with both an α-emitting radionuclide (e.g. Astatine 211 or Actinium-225) and a macromolecule (e.g. a PEG, a dextran or a FICOLL®); for attenuating the specific damage to remaining healthy renal tissue and unspecific damage to other tissues.

In this embodiment Orellanine is first conjugated to a macromolecule by any of the methods mentioned in the above description of the first embodiment of the invention. This conjugate, rather than Orellanine itself, is then used as starting material in the astatine-conjugating reaction in the above description of the second embodiment of the invention. Preferably, the macromolecule is conjugated to the 5-position of the Orellanine molecule, and the astatine is conjugated to the 5'-position.

Conjugation of a compound/form (or similar) according to Formula I in the specification is defined as a conjugation of a compound according to Formula I in line with one or several of the described three embodiments of the invention.

The present invention provides a method for treating a patient suffering from or susceptible to renal cell carcinoma in which the method comprises the step of administering to the patient a conjugated form of Formula I, a pharmaceutically acceptable salt thereof or a pharmaceutical composition comprising said compound.

The conjugated molecule that is administered to a patient comprises a compound of Formula I in which R1, R2, R3 and/or R4 do not cause substantially different cytotoxicity, specificity or uptake into renal cancer cells compared to unconjugated Orellanine (R1=R2=R3=R4=hydrogen). Thus, R1, R2, R3 and/or R4 include, but are not limited to, hydrogen, amino, mercapto, carboxy, phosphate and halo, including fluoro, chloro, and bromo, $C_1$-$C_6$ alkyl, $C_1$-$C_6$ alkenyl, $C_1$-$C_6$ alkynyl, $C_1$-$C_6$ alkanol, $C_1$-$C_6$ alkenol, $C_1$-$C_6$ alkoxy, $C_1$-$C_6$ alkenoxy, each of which may be further substituted with groups including but not limited to amino, mercapto, carboxy, phosphate and halo, including fluoro, chloro, and bromo. In a preferred embodiment of the present invention, the unconjugated compound of Formula I is orellanine, i.e. R1=R2=R3=R4=hydrogen. The conjugation of one or several macromolecules and/or one or several alpha-emitting radionuclides can be performed at any of the positions R1, R2, R3 and R4, as well as at any other substituent of a compound of Formula I, in any possible combination. Thus, conjugation of the macromolecule and/or the radionuclide to any of the hydroxyl groups in Formula I is possible without deviating from the scope of the invention. In the corresponding preferred conjugated compound according to Formula I, R1 is a macromolecule, selected from the group comprising dextrans, polyethylene glycols and Ficolls, and R3 is an alpha-emitting radionuclide, selected from the group comprising Astatine-211, Bismuth-212, Bismuth-213, Actinium-225, Lead-212 and Terbium-149.

In a further embodiment of the methods according to the present invention of treating patients suffering from or susceptible to renal cancer, the conjugated compound of Formula I administered to the patient is a pharmaceutically acceptable salt, hydrate, or solvate. As used herein, a pharmaceutically acceptable salt is an acid or base salt that is generally considered in the art to be suitable for use in contact with the tissues of human beings or animals without excessive toxicity, irritation, allergic response, or other problems or complications. Such salts include mineral and organic acid salts of basic residues, such as amines. Specific pharmaceutical salts include, but are not limited to, salts of acids such as hydrochloric, phosphoric, hydrobromic, malic, glycolic, fumaric, sulfuric, sulfamic, sulfanilic, formic, toluenesulfonic, methanesulfonic, benzene sulfonic, ethane disulfonic, 2-hydroxyethylsulfonic, nitric, benzoic, 2-acetoxybenzoic, citric, tartaric, lactic, stearic, salicylic, glutamic, ascorbic, pamoic, succinic, fumaric, maleic, propionic, hydroxymaleic, hydroiodic, phenylacetic, alkanoic such as acetic, HOOC—(CH2)n-COOH where n is 0-4, and the like.

In the methods of treating renal cancer provided herein, the conjugated compound of Formula I can be administered in a single dose, in a series of daily doses or in an intermittent dosing format (e.g., a plurality of doses or dose sequences administered between 1 and about 30 days apart, between 1 and about 14 days apart or between 1 and about 7 days apart). In certain methods, the administration protocol and conjugated compound of Formula I are selected to provide at least a 50% reduction in tumor size, or more preferably at least a 75%, 90%, or 95% reduction in tumor size after completion of the administration protocol, while in certain other methods, selection of the administration protocol and conjugated compound of Formula I result in a 95% reduction in tumor size, a 99% reduction in tumor size or a substantially complete elimination of the tumor.

In the methods of treatment, according to the first embodiment of the invention, that comprise a single dose administration protocol, a single dose of conjugated compound according to Formula I corresponding to an amount of unconjugated Orellanine between about 1 mg/kg and about 100 mg/kg, or an equivalent molar amount of a pharmaceutically acceptable salt thereof, is administered to the patient, while a preferred single dose for administration to the patient corresponds to between about 2 mg/kg and about 25 mg/kg of unconjugated Orellanine, most preferably between about 5 mg/kg and about 15 mg/kg of unconjugated Orellanine, or an equivalent molar amount of a pharmaceutically acceptable salt thereof.

In the methods of treatment, according to the second and third embodiments of the invention, that comprise a single dose administration protocol, a single dose of conjugated compound according to Formula I corresponding to an amount of unconjugated Orellanine between about 0.1 mg/kg and about 20 mg/kg, or an equivalent molar amount of a pharmaceutically acceptable salt thereof, is administered to the patient, while a preferred single dose for administration to the patient corresponds to between about 0.2 mg/kg and about 5 mg/kg of unconjugated Orellanine, most preferably between about 0.5 mg/kg and about 2 mg/kg of unconjugated Orellanine, or an equivalent molar amount of a pharmaceutically acceptable salt thereof.

In certain other therapeutic methods of treating renal cancer according to the first embodiment of the invention, a conjugated compound of Formula I, or a pharmaceutically acceptable salt thereof is administered to the patient suffering from or susceptible to renal cancer in two or more doses. Typically the doses are administered daily or intermittently (e.g., with at least one non-administration day separating sequential doses). In certain methods in which the conjugated compound of Formula I, or a pharmaceutically acceptable salt thereof is administered in a plurality of doses, each dose comprises an amount of conjugated compound according to Formula I corresponding to between about 0.5 mg/kg and about 10 mg/kg of unconjugated Orellanine, or more preferably, each dose comprises an amount of conjugated compound according to Formula I corresponding to between about 1 mg/kg and about 5 mg/kg, or most preferably about 2 mg/kg of unconjugated Orellanine.

In certain other therapeutic methods of treating renal cancer according to the second and third embodiments of the invention, a conjugated compound of Formula I, or a pharmaceutically acceptable salt thereof is administered to the patient suffering from or susceptible to renal cancer in two or more doses. Typically the doses are administered daily or intermittently (e.g., with at least one non-administration day separating sequential doses). In certain methods in which the conjugated compound of Formula I, or a pharmaceutically acceptable salt thereof is administered in a plurality of doses, each dose comprises an amount of conjugated compound according to Formula I corresponding to between about 0.05 mg/kg and about 2 mg/kg of unconjugated Orellanine, or more preferably, each dose comprises an amount of conjugated compound according to I corresponding to between about 0.01 mg/kg and about 1 mg/kg, or most preferably about 0.2 mg/kg of unconjugated Orellanine.

In certain methods according to the first embodiment of the invention, in which sequential doses are administered intermittently, the sequential doses are administered between two and seven days apart, in yet other methods comprising intermittent administration of the compound or salt of Formula I, the compound is administered to the patient in three, four, five or six or more doses and wherein each dose is administered between three and five days apart, in yet other methods, the patient is administered four, five, or six or more doses administered between three and four days apart, wherein each dose comprises an amount of conjugated compound according to Formula I corresponding to between about 1 mg/kg and about 20 mg/kg of unconjugated Orellanine, preferably 2-10 mg/kg and most preferably about 5 mg/kg of unconjugated Orellanine, or a pharmaceutically acceptable salt thereof. In certain other therapeutic methods of treating renal cancer the patient is administered a daily dose of a conjugated compound of Formula I, or a pharmaceutically acceptable salt thereof, for at least two days. Typical daily doses administered to patients comprise an amount of conjugated compound according to Formula (I) corresponding to between 0.1 and 10 mg/kg of unconjugated Orellanine, preferably between 1 and 5 mg/kg, and most preferably about 2 mg/kg of unconjugated Orellanine. Therapeutic protocols typically comprise daily administration of the conjugated compound of Formula I, or a pharmaceutically acceptable salt thereof, between 5 and about 30 days, or preferably between 10 and 20 days, or most preferably about 14 days.

In certain methods according to the second and third embodiment of the invention, in which sequential doses are administered intermittently, the sequential doses are administered between two and seven days apart, in yet other methods comprising intermittent administration of the compound or salt of Formula I, the compound is administered to the patient in three, four, five or six or more doses and wherein each dose is administered between three and five days apart, in yet other methods, the patient is administered four, five, or six or more doses administered between three and four days apart, wherein each dose comprises an amount of conjugated compound according to Formula I corresponding to between about 0.1 mg/kg and about 4 mg/kg of unconjugated Orellanine, preferably 0.2-2 mg/kg and most preferably about 0.5 mg/kg of unconjugated Orellanine, or a pharmaceutically acceptable salt thereof. In certain other therapeutic methods of treating renal cancer the patient is administered a daily dose of a conjugated compound of Formula I, or a pharmaceutically acceptable salt thereof, for at least two days. Typical daily doses administered to patients comprise an amount of conjugated compound according to Formula I corresponding to between 0.01 and 2 mg/kg of unconjugated Orellanine, preferably between 0.01 and 1 mg/kg, and most preferably about 0.25 mg/kg of unconjugated Orellanine. Therapeutic protocols typically comprise daily administration of the conjugated compound of Formula I, or a pharmaceutically acceptable salt thereof, between 5 and about 30 days, or preferably between 10 and 20 days, or most preferably about 14 days.

In certain instances, it may be desirable to conduct a plurality of intermittent administration protocols, daily administration protocols, or a combination thereof, as described above, in combination with rest and/or recovery periods. Thus, in certain instances, it may be desirable to administer a conjugated compound of Formula I, or a pharmaceutically acceptable salt thereof, according to a daily or intermittent administration method provided herein, measure the tumor response to the therapy, and then conduct subsequent daily or intermittent administration therapies as necessary to eliminate or further reduce the size of the renal cancer tumors. Such administration strategies are well known to the person with normal skills in the field of oncology.

In one particularly preferred aspect of the first embodiment of the present invention a patient suffering from renal cell carcinoma is treated with the conjugated compound according to Formula I of the present invention by daily injections of amounts of conjugated compound according to Formula I corresponding to about 0.5-5 mg unconjugated Orellanine/kg b.w., most preferably about 2 mg unconjugated Orellanine/kg b.w., for about 7-21 consecutive days, most preferably about 14 consecutive days. One to 5 hours after each daily injection of a conjugated compound according to Formula 1, most preferably about 2 hours after such injection, the patient is subjected to hemodialysis for 1-5 h, most preferably about 2 h, in order to eliminate any compound according to Formula 1 that has not been taken up into tumor tissue and thereby minimize any undesired side effects that might occur in the extracellular space.

In one particularly preferred aspect of the second and third embodiments of the present invention a patient suffering from renal cell carcinoma is treated with the conjugated compound according to Formula I of the present invention by daily injections of amounts of conjugated compound according to Formula I corresponding to about 0.05-1 mg unconjugated Orellanine/kg body weight (b.w.), most preferably about 0.3 mg unconjugated Orellanine/kg b.w., for about 7-21 consecutive days, most preferably about 14 consecutive days. One to 5 hours after each daily injection of a conjugated compound according to Formula I, most preferably about 2 hours after such injection, the patient is subjected to hemodialysis for 1-5 h, most preferably about 2 h, in order to eliminate any compound according to Formula I that has not been taken up into tumor tissue and thereby minimize any undesired side effects that might occur in the extracellular space.

The preferred doses and dose regimes described above are based on a human being weighing 70 kg and suffering from renal cell carcinoma with a tumor burden of about 1 kg. However, as is readily known to the worker with normal skills in the field of cancer medicine, such preferred doses and dose regimes are governed to a large extent by patient characteristics such as age, sex, weight, general condition and, above all, the individual patient's tumor burden and response to the treatment. As always, the ultimate responsibility for choosing the proper dose and treatment strategy lies with the physician in charge of the patient.

The invention provides methods of treating patients suffering from or susceptible to renal cell carcinoma. The methods of the invention fall into either of three main embodiments. The first embodiment is most preferred in cases when the patient has remaining renal function after surgical treatment (i.e. unilateral disease or bilateral disease with kidney-sparing surgery) and for some reason cannot tolerate treatment with radionuclides. The second embodiment of the invention is most preferred when the patient has no remaining renal function after surgical treatment (i.e. bilateral disease and radical nephrectomy). This occurs in up to 5% of the patient population. The third embodiment of the invention is most preferred when the patient has remaining renal function (i.e. unilateral disease or bilateral disease with kidney-sparing surgery) that needs to be protected against Orellanine toxicity.

In certain cases, the renal cell carcinoma has metastasized, e.g., at least one renal cell carcinoma tumor is present in at least one non-kidney tissue. Typically the methods provided herein are suitable for use in the treatment of patients suffering from or susceptible to renal cell carcinoma tumors that are present in the kidneys, in non-kidney tissues, or in a combination thereof. In a preferred embodiment, the tumors are present in non-kidney tissues or in a combination of kidney and non-kidney tissues. The methods of treatment provided by the instant invention contemplate any administration pathway capable of delivering a therapeutically effective dose of a conjugated compound of Formula I to the vicinity of the tumor. In certain preferred methods of treatment provided herein, the conjugated compound of Formula I, or a pharmaceutical composition comprising the same is administered intravenously, subcutaneously, or intraperitoneally. Typically the conjugated compound of Formula I, or a pharmaceutical composition comprising the same is administered intravenously.

In another aspect, the invention provides conjugated compounds of Formula I, wherein R1, R2, R3 and/or R4 do not cause substantially different cytotoxicity, specificity or uptake into renal cancer cells compared to unconjugated Orellanine (R1=R2=R3=R4=hydrogen), for use as a medicament. The invention also provides the use of conjugated compounds of Formula I, wherein R1, R2, R3 and/or R4 do not cause substantially different cytotoxicity, specificity or uptake into renal cancer cells compared to unconjugated Orellanine (R1=R2=R3=R4=hydrogen), as a medicament. R1, R2, R3 and/or R4 include, but are not limited to, hydrogen, amino, mercapto, carboxy, phosphate and halo, including fluoro, chloro, and bromo, $C_1$-$C_6$ alkyl, $C_1$-$C_6$ alkenyl, $C_1$-$C_6$ alkynyl, $C_1$-$C_6$ alkanol, $C_1$-$C_6$ alkenol, $C_1$-$C_6$ alkoxy, $C_1$-$C_6$ alkenoxy, each of which may be further substituted with groups including but not limited to amino, mercapto, carboxy, phosphate and halo, including fluoro, chloro, and bromo. In a preferred embodiment of the present invention, the unconjugated compound of Formula I is Orellanine, i.e. R1=R2=R3=R4=hydrogen. In the corresponding preferred conjugated compound according to Formula I, R1 is a macromolecule, selected from the group comprising dextrans, polyethylene glycols and Ficolls, and R3 is an alpha-emitting radionuclide, selected from the group comprising Astatine-211, Bismuth-212, Bismuth-213, Actinium-225, Lead-212 and Terbium-149. Other preferred embodiments of this aspect of the invention are evident from the detailed description.

In yet another aspect, the invention provides conjugated compounds of Formula I, wherein R1, R2, R3 and/or R4 do not cause substantially different cytotoxicity, specificity or uptake into renal cancer cells compared to unconjugated Orellanine (R1=R2=R3=R4=hydrogen), for use in the treatment of renal cell carcinoma. The invention also provides the use of conjugated compounds of Formula I, wherein R1, R2, R3 and/or R4 do not cause substantially different cytotoxicity, specificity or uptake into renal cancer cells compared to unconjugated Orellanine (R1=R2=R3=R4=hydrogen), for the manufacture of a medicament for the treatment of renal cell carcinoma. R1, R2, R3 and/or R4 include, but are not limited to, hydrogen, amino, mercapto, carboxy, phosphate and halo, including fluoro, chloro, and bromo, $C_1$-$C_6$ alkyl, $C_1$-$C_6$ alkenyl, $C_1$-$C_6$ alkynyl, $C_1$-$C_6$ alkanol, $C_1$-$C_6$ alkenol, $C_1$-$C_6$ alkoxy, $C_1$-$C_6$ alkenoxy, each of which may be further substituted with groups including but not limited to amino, mercapto, carboxy, phosphate and halo, including fluoro, chloro, and bromo. In a preferred embodiment of the present invention, the unconjugated compound of Formula I is orellanine, i.e. R1=R2=R3=R4=hydrogen. In the corresponding preferred conjugated compound according to Formula I, R1 is a macromolecule, selected from the group comprising dextrans, polyethylene glycols and Ficolls, and R3 is an alpha-emitting radionuclide, selected from the group comprising Astatine-211, Bismuth-212, Bismuth-213, Actinium-225, Lead-212 and Terbium-149. Other preferred embodiments of this aspect of the invention are evident from the detailed description.

In another aspect, the invention provides a pharmaceutical composition comprising at least one pharmaceutically acceptable carrier and a conjugated compound according to the Formula I, wherein R1, R2, R3 and/or R4 do not cause substantially different cytotoxicity, specificity or uptake into renal cancer cells compared to unconjugated Orellanine (R1=R2=R3=R4=hydrogen). Thus, R1, R2, R3 and/or R4 are exemplified by, but not limited to, hydrogen, amino, mercapto, carboxy, phosphate and halo, including fluoro, chloro, and bromo, $C_1$-$C_6$ alkyl, $C_1$-$C_6$ alkenyl, $C_1$-$C_6$ alkynyl, $C_1$-$C_6$ alkanol, $C_1$-$C_6$ alkenol, $C_1$-$C_6$ alkoxy, $C_1$-$C_6$ alkenoxy, each of which may be further substituted with groups including but not limited to amino, mercapto, carboxy, phosphate and halo, including fluoro, chloro, and bromo. In a preferred embodiment of the present invention, the unconjugated compound of Formula I is orellanine, i.e. R1=R2=R3=R4=hydrogen. In the corresponding preferred conjugated compound according to Formula I, R1 is a macromolecule, selected from the group comprising dextrans, polyethylene glycols and Ficolls, and R3 is an alpha-emitting radionuclide, selected from the group comprising Astatine-211, Bismuth-212, Bismuth-213, Actinium-225, Lead-212 and Terbium-149.

In certain other pharmaceutical compositions, the conjugated compound of Formula I is incorporated into the composition as a pharmaceutically acceptable salt, hydrate, or solvate. As used herein, a pharmaceutically acceptable salt is an acid or base salt that is generally considered in the art to be suitable for use in contact with the tissues of human beings or animals without excessive toxicity, irritation, allergic response, or other problem or complication. Such salts include mineral and organic acid salts of basic residues such as amines. Specific pharmaceutical salts include, but are not limited to, salts of acids such as hydrochloric, phosphoric, hydrobromic, malic, glycolic, fumaric, sulfuric, sulfamic, sulfanilic, formic, toluenesulfonic, methanesulfonic, benzene sulfonic, ethane disulfonic, 2-hydroxyethylsulfonic, nitric, benzoic, 2-acetoxybenzoic, citric, tartaric, lactic, stearic, salicylic, glutamic, ascorbic, pamoic, succinic, fumaric, maleic, propionic, hydroxymaleic, hydroiodic, phenylacetic, alkanoic such as acetic, HOOC—$(CH2)_n$—COOH where n is 0-4, and the like.

The pharmaceutical compositions provided by the instant invention are suitable for use in any administration pathway contemplated by the methods of treatment in which the compositions will be used. In the methods of the invention, conjugated compounds of the invention according to Formula I and pharmaceutical compositions thereof may be administered to a subject by a variety of routes including parenteral (including intravenous, subcutaneous, intramuscular and intradermal), topical (including buccal, sublingual), oral, nasal and the like. In certain preferred pharmaceutical compositions provided herein, the pharmaceutical composition is formulated for administration by intravenous, subcutaneous, or intraperitoneal injection. Typically the pharmaceutical composition is formulated for administration by intravenous injection.

In certain parenteral administration routes, the pharmaceutical composition is a sterile saline solution comprising an amount of conjugated compound according to Formula I that corresponds to between about 0.1 mg/mL to about 25 mg/mL of unconjugated Orellanine according to the first embodiment of the invention and about 0.01 mg/mL to about 5 mg/mL of unconjugated Orellanine according to the second and third embodiments of the invention, or a pharmaceutically acceptable salt thereof. Certain preferred pharmaceutical compositions for parenteral administration comprise an amount of conjugated compound according to Formula I that corresponds to between about 0.5 mg/mL to about 10 mg/mL of unconjugated Orellanine according to the first embodiment of the invention and about 0.05 mg/mL to about 2 mg/mL of unconjugated Orellanine according to the second and third embodiments of the invention, or an equivalent molar amount of pharmaceutically acceptable salt thereof in a saline solution which optionally comprises one or more pharmaceutically acceptable additives.

In certain preferred pharmaceutical compositions, the composition comprises an amount of conjugated compound according to Formula I that corresponds to between about 25 mg and about 5000 mg or between about 5 mg and about 2500 mg of unconjugated Orellanine according to the first embodiment of the invention, and between about 2.5 mg to about 1000 mg or between about 0.5 mg to about 500 mg of unconjugated Orellanine according to the second and third embodiments of the invention, or an equivalent molar amount of a pharmaceutically acceptable salt thereof. In certain other pharmaceutical compositions of the invention, the composition comprises an amount of conjugated compound according to Formula I that corresponds to between about 1 mg to about 1500 mg of unconjugated Orellanine according to the first embodiment of the invention, and between about 0.1 mg to about 300 mg of unconjugated Orellanine according to the second and third embodiments of the invention, or an equivalent molar amount of a pharmaceutically acceptable salt thereof. Yet other pharmaceutical compositions are formulated to comprise an amount of conjugated compound according to Formula I that corresponds to about 20 mg, about 30 mg, about 40 mg, about 50 mg, about 60 mg, about 70 mg, about 80 mg, about 90 mg, or about 100 mg of unconjugated Orellanine according to the first embodiment of the invention, and about 2 mg, about 3 mg, about 4 mg, about 5 mg, about 6 mg, about 7 mg, about 8 mg, about 9 mg, or about 10 mg of unconjugated Orellanine according to the second and third embodiments of the invention, or an equivalent molar amount of a pharmaceutically acceptable salt thereof.

In certain methods of treating a patient suffering from or susceptible to cancer, the administration of the conjugated compound according to Formula I to a patient suffering from or susceptible to cancer decreases tumor size by at least 50% or more preferably by at least about 60%, 70%, 80%, 90% or about 95%. In certain other methods of treating a patient suffering from cancer, the administration of the conjugated compound according to Formula I to a patient suffering from cancer decreases tumor size by at least 99% or decreases tumor size until no detectable tumor remains.

Certain preferred methods of treating patients suffering from cancer include treatment or prevention of cancer or other tumor disorders in mammalian patients including livestock, companion animals (dogs, cats, horses and the like), primates and humans.

Treatment methods of the invention include in general administration to a patient a therapeutically effective amount of one or more conjugated compounds of Formula I. In the instant therapeutic methods, a therapeutically effective amount is sufficient to reduce the size of renal cell carcinoma tumors present in a patient or to eliminate tumors from the patient. Suitable patients include those subjects suffering from a disorder or disease identified herein. Typical patients for treatment in accordance with the invention include mammals, particularly primates, especially humans. Other suitable subjects include domesticated companion animals such as a dog, cat, horse, and the like, or a livestock animal such as cattle, pig, sheep and the like.

Preferred methods of the invention include identifying and/or selecting a subject (e.g. mammal, particularly human) that is suffering from a condition disclosed herein, particularly a subject that is suffering from one or more cancers. A pharmaceutical composition of the invention also may be packaged together with instructions (i.e. written, such as a written sheet) for treatment of a cancer as disclosed herein, e.g. instruction for treatment of a subject that is suffering from cancer.

Compounds of the invention are suitably administered to a subject in a water-soluble form, e.g., as a pharmaceutically acceptable salt of an organic or inorganic acid, e.g., hydrochloride, sulfate, hemi-sulfate, phosphate, nitrate, acetate, oxalate, citrate, maleate, mesylate, etc obtained after proper chemical transformation. Also, where an acidic group is present on the compound, a pharmaceutically acceptable salt of an organic or inorganic base can be employed, such as an ammonium salt, or salt of an organic amine, or a salt of an alkali metal or alkaline earth metal such as a potassium, calcium or sodium salt. Specifically suitable pharmaceutically acceptable salts include those formed with a non-toxic cation, preferably an alkali metal cation such as K or Na, an alkaline earth metal cation such as Mg or Ca, another non-toxic metal cation such as Al or Zn or a non-toxic metalloid cation such as $NH_4^+$, piperazinium or 2-hydroxyethylammonium. Certain preferred compounds suitable for use in the methods of the invention are sufficiently water-soluble in neutral form in such a way that they may be delivered without pre-generation of a pharmaceutically acceptable salt.

Compounds suitable for use in the methods of the present invention include any and all different single pure isomers and mixtures of two or more isomers. The term isomers is intended to include diastereoisomers, enantiomers, regioisomers, structural isomers, rotational isomers, tautomers, and the like. For compounds that contain one or more stereogenic centers, e.g., chiral compounds, the methods of the invention may be carried out with an enantiomerically enriched compound, a racemate, or a mixture of diastereomers. Preferred enantiomerically enriched compounds have an enantiomeric excess of 50% or more, more preferably the compound has an enantiomeric excess of 60%, 70%, 80%, 90%, 95%, 98%, or 99% or more. Conjugated compounds of the invention according to Formula I for use in the methods of the invention can be employed, either alone or in combination with one or more other therapeutic agents, as a pharmaceutical composition in mixture with conventional excipients, i.e., pharmaceutically acceptable organic or inorganic carrier substances suitable for a desired route of administration which do not deleteriously react with the active compounds and are not deleterious to the recipient thereof. Suitable pharmaceutically acceptable carriers include but are not limited to water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethyl-cellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously react with the active compounds.

For parenteral application, solutions, preferably oily or aqueous solutions as well as suspensions, emulsions, or implants, including suppositories, are particularly suitable. Ampoules are convenient unit dosages.

It should be understood that in addition to the ingredients explicitly mentioned above the formulations of this invention might include other agents conventional in the art with regard to the type of formulation in question.

According to certain embodiments, a conjugated compound of Formula I may be administered in combination with other compounds, including for example, chemotherapeutic agents, anti-inflammatory agents, anti-pyretic agents radiosensitizing agents, radioprotective agents, urologic agents, anti-emetic agents, and/or anti-diarrheal agents, for example, cisplatin, carboplatin, docetaxel, paclitaxel, flurouracil, capecitabine, gemcitabine, irinotecan, topotecan, etoposide, mitomycin, gefitinib, vincristine, vinblastine, doxorubicin, cyclophosphamide, celecoxib, rofecoxib, valdecoxib, ibuprofen, naproxen, ketoprofen, dexamethasone, prednisone, prednisolone, hydrocortisone, acetaminophen, misonidazole, amifostine, tamsulosin, phenazopyridine, ondansetron, granisetron, alosetron, palonosetron, promethazine, prochlorperazine, trimethobenzamide, aprepitant, diphenoxylate with atropine, and/or loperamide. In one preferred embodiment the conjugated compound according to Formula I is administered in combination with antiangiogenetic drugs, including for example monoclonal antibodies directed against Vascular Endothelial Growth Factor (VEGF) and Placental Growth Factor (PlGF); and inhibitors of the VEGF and PlGF receptors, including for example bevacizumab, sorafenib, PTK78, SU11248, AG13736, AEE788, and ZD6474. In another embodiment the compound according to Formula I is administered in combination with immunomodulatory drugs, including for example interleukin 2 (IL-2) and Interferon alpha (IFN-α). In yet another embodiment a conjugated compound according to Formula I is administered in combination with drugs interfering with cellular growth signaling, including for example inhibitors of the mammalian target of rapamycin (mTOR).

In yet other embodiments of the present invention the conjugated compounds according to Formula I are chemically bound to molecules that enhance the target selectivity even further by targeting the compounds of Formula I specifically to cancerous cells. Examples of such molecules include (A) polyclonal and monoclonal antibodies directed against markers occurring specifically or in greater numbers on the target cells compared to normal renal tissue, and (B) ligands to receptors occurring specifically or in greater numbers on the target cells compared to normal renal tissue. Such guidance molecules, and techniques for conjugating them to the compounds in the invention are known in the art; and coupling reactions can be performed by the normally skilled artisan without undue experimentation.

The kit of the invention herein comprises at least one pharmaceutically acceptable carrier and an amount of a conjugated compound according to Formula I that corresponds to 50 to 3,500 mg (first embodiment of the invention) or 5 to 500 mg (second and third embodiments of the invention) of unconjugated Orellanine, or the equivalent molar amount of a pharmaceutically acceptable salt thereof, as discussed above. In the kit the conjugated compound according to Formula I or acceptable salt thereof and the pharmaceutically acceptable carrier are preferably located in separate compartments. In one aspect the kit further comprises at least one reagent required for attachment of an alpha-emitting radionuclide to the non-radioactive compound according to Formula I in immediate connection to administration of the compound of the invention. The compound according to Formula I is preferably present in the kit as a solid. For administration, the compound according to Formula I or pharmaceutically acceptable salt thereof is preferably combined with the carrier and/or reagents necessary to effect attachment of an alpha-emitting radionuclide so that it is completely or substantially dissolved in the carrier. The kit may comprise an amount of a conjugated compound according to Formula I that corresponds to between about 100 mg to about 1,500 mg, and most preferably between about 200 mg to about 500 mg, of unconjugated Orellanine in the first embodiment of the invention, or an amount of a conjugated compound according to Formula I that corresponds to between about 10 mg to about 200 mg, and most preferably between about 20 mg to about 70 mg, of unconjugated Orellanine in the second and third embodiments of the invention, or an equivalent molar amount of a pharmaceutically acceptable salt thereof.

The foregoing description of the invention is merely illustrative thereof, and it is understood that variations and modifications can be effected without departing from the spirit or scope of the invention. Each of the documents referred to herein is incorporated by reference into the disclosure of the application.

EXAMPLES

Example 1

Synthesis of Orellanine

Orellanine was synthesized from commercially available 3-hydroxypyridine essentially as described by others. (Tiecco M, Tingoli M, Testaferri L, Chianelli D and Wenkert E: Total synthesis of Orellanine, the lethal toxin of *Cortinarius orellanus* Fries Mushroom. *Tetrahedron* 42, 1475-1485 (1986).

Example 2

Conjugating Orellanine to Polyethylene Glycol (PEG)

A. Conjugation on Carbon.

A solution of lithium diisopropylamide (LDA) is prepared at −23° C. from diisopropylamine (0.77 ml, 5.50 mmol) and 1.55 M n-butyllithium (3.55 ml, 5.50 mmol) in 10 ml of tetrahydrofuran (THF). After 15 min 3,3',4,4'-tetramethoxy-2,2'-bipyridine-di-N-oxide (1.54 g, 5.00 mmol) is added and the resulting mixture is stirred at −23 for 30 min. 1-Bromo-2-(2-methoxyethoxy)ethane (1.19 g, 6.50 mmol) is added and the reaction mixture is stirred at −23° C. for 15 min and at room temperature for 1 hr. Water (10 ml) and diethylether (10 ml) are added, and the layers are separated. The aqueous phase is extracted with diethylether (3×25 ml). The combined organic extracts are washed with 25 ml portions of water and brine. After drying over anhydrous $Na_2SO_4$, the solvent is removed in vacuo to give the crude product. Purification by flash chromatography (SiO2, 25% EtOAc in hexane) gives 1.23 g (60%) of the monoalkylated Orellanine derivative as white crystals.

B. Conjugation on Oxygen.

252 mg, 1 mmol, Orellanine and 636 mg sodium carbonate, 6 mmol, is dissolved in 25 ml water. 52.3 mg. A solution of 5% Aliquat 336 in 25 ml dichloromethane is added and the mixture is vigorously stirred. 275 mg 1-bromo-2-(2-methoxyethoxy)ethane, 1.5 mmol, is added drop wise and the mixture is stirred for 2 hrs. The phases are separated and the organic phase is washed with alkaline water. The combined water phases are neutralized and the monoalkylated Orellanine is isolated by preparative HPLC.

All chemicals are purchased from local dealers except for Orellanine that is synthesized according to Example 1.

Analogously an Orellanine derivatized with brominated MPEG5000 (mono-methoxypolyethyleneglycol) is prepared.

Analogously an Orellanine derivatized with brominated ethoxylated Ficoll is prepared.

Analogously an Orellanine derivatized with brominated ethoxylated dextran is prepared.

Example 3

Labeling of Orellanine with Astatine 211 (At-211)

13 mg, 0.051 mmol, Orellanine and 32.8 mg sodium carbonate, 0.3 mmol, are dissolved in 1.2 ml water. IodoGen beads (Thermo Fisher Scientific, Rockford, Ill.) are added and then 0.20 mmol, radioactive iodine in the form of NaI. The mixture is stirred for 90 minutes at room temperature. Then the mixture is filtered to remove the IodoGen beads and the filtrate is acidified with 42 mg NaHSO4. The labelled Orellanine is isolated by preparative HPLC.

Analogously an Orellanine derivative radiohalogenated with [211]At, produced by irradiation of natural Bi with 28 MeV alfa particles, is prepared, purified by distillation and collected in Teflon tubes. All standard chemicals are purchased from local dealers except for Orellanine that is synthesized according to Example 1.

Example 4

Labeling of PEG-Conjugated Orellanine with Astatine 211 (At-211)

Orellanine, synthesized as described in Example 1, is conjugated to PEG at the 5 position as described in Example 2, and subsequently radiohalogenated with [211]At according to example 3 at the 5'-position.

Example 5

Renal Function After Administration of PEG-Conjugated Orellanine

Background and Methodology

6 Sprague-Dawley rats weighing ~150 g are injected intravenously with PEG-conjugated Orellanine corresponding to 5 mg Orellanine/kg. Four days later the animals are anesthetized and surgically prepared for measurement of renal function (glomerular filtration rate, GFR) according to previously described procedures (Andersson M. et al.: Am J Physiol Renal Physiol. (2007), 292:F1802-9).

Results and Comments

All 6 rats have preserved a substantial part of their renal function, i.e. at least 50% of normal GFR (1 ml/min×g kidney tissue) remains. On the contrast, it is known (Nilsson U A et al.: Free Radic Biol Med. (2008) 44:1562-9) that corresponding amounts of unconjugated Orellanine administered to Sprague-Dawley rats leads to almost total loss of GFR within four days.

Example 6

Effect of PEG-Conjugated Orellanine on Cultured Renal Cell Carcinoma

Background and Methodology

Cells harvested from 2 different human renal cell carcinomas (SKRC-7, 786-0), representing both mother tumors and metastatic growths, are cultured under standard conditions. When approximately 70% confluent and in rapid growth, the cells are exposed for 24 h to medium containing different concentrations of either Orellanine or corresponding concentrations of PEG-conjugated Orellanine. Then the medium is changed back to regular, complete medium and the cells are observed for another six days.

Results and Comments

A clear correlation is seen between the exposure concentration and the fraction of cells that die, both for unconjugated and PEG-conjugated Orellanine. The dose response interval for a single 24 h-exposure of Orellanine is between approximately 5 µg/ml and 200 µg/l for unconjugated Orellanine, and does not differ significantly for the PEG-conjugated Orellanine.

This demonstrates that PEG-conjugated Orellanine is taken up into the carcinoma cells to a degree that allows efficient killing of the cancer cells.

Example 7

Effect of Astatine 211-Labeled Orellanine on Cultured Renal Cell Carcinoma

Background and Methodology

Cells harvested from 2 different human renal cell carcinomas (SKRC-7, 786-0), representing both mother tumors and metastatic growths, are cultured under standard conditions. When approximately 70% confluent and in rapid growth, the cells are exposed for 24 h to medium containing different concentrations of either unlabeled Orellanine or At-211-labeled Orellanine. Then the medium is changed back to regular, complete medium and the cells are observed for another six days.

Results and Comments

A clear correlation is seen between the exposure concentration and the fraction of cells that die, both for unlabeled and At-211-labeled Orellanine. The dose response interval for a single 24 h-exposure of Orellanine is between approximately 5 µg/ml and 200 µg/l for unlabeled Orellanine. For Orellanine labeled with At-211, however the interval is shifted towards lower concentrations by one order of magnitude. Furthermore, the delay between administration of Orellanine and onset of cell death is reduced from 48 h for unlabeled Orellanine to just a few hours for the At-211-labeled Orellanine due to the rapid α-emitting decay of the At-211 (half-life 7.5 h).

Example 8

Effect of PEG-Conjugated and Astatine 211-Labeled Orellanine on Cultured Renal Cell Carcinoma Background and Methodology Cells harvested from 2 different human renal cell carcinomas (SKRC-7, 786-0), representing both mother tumors and metastatic growths, are cultured under standard conditions. When approximately 70% confluent and in rapid growth, the cells are exposed for 24 h to medium containing different concentrations of either $^{211}$At-Orellanine or corresponding concentrations of PEG-conjugated $^{211}$At-Orellanine. Then the medium is changed back to regular, complete medium and the cells are observed for another six days.

Results and Comments

A clear correlation is seen between the exposure concentration and the fraction of cells that die, both for unconjugated and PEG-conjugated $^{211}$At-Orellanine. The dose response interval for a single 24 h-exposure of Orellanine is between approximately 5 µg/ml and 200 µg/l for unconjugated Orellanine, and does not differ significantly for the PEG-conjugated Orellanine.

Example 9

Effect of PEG-Conjugated Orellanine In-Vivo in a Rat Model of Renal Cell Carcinoma Background and Methodology Athymic, T cell-deficient rats (RNU, Charles River Laboratories, FRG) are used as a system for in vivo-growth of human renal cell carcinomas. The absence of a T cell-based immune defense in these animals makes them tolerant towards xenografts. One week after arrival in the animal facility 12 animals receive an X-irradiation dose of 5 Gy in order to suppress also their B cell-mediated response.

Three days later the animals are inoculated subcutaneously in the shoulder region with approximately 10×10$^6$ human renal carcinoma cells (SKRC-52). After several days, when localized tumors are palpable under the animals' skin, 6 animals are surgically equipped with an indwelling catheter for peritoneal dialysis (PD). (PD treatment will replace the renal function that is lost as a side effect upon administration of Orellanine.) After the surgical procedure each of these 6 animals receives an amount of PEG-conjugated Orellanine corresponding to 5 mg/kg unconjugated Orellanine intravenously. The following day, dialysis is started via the PD-catheter. The dialysis fluid entering the animals via the catheter is supplemented for the first 48 h with PEG-conjugated Orellanine corresponding to 10 mg Orellanine/L dialysis fluid. The animals receive PD with PEG-conjugated Orellanine for two consecutive days, each day consisting of four dialysis cycles of 15 mL of PD-fluid that is allowed to dwell in the abdominal cavity for 60 min, followed by an emptying phase of 30 min. The same regimen is followed for another 12 days, but without any Orellanine in the PD-fluid.

Five days after treatment is completed the subcutaneous tumors are visually inspected through the skin. One week later the experiment is terminated and the tumors are excised, and at the same occasion measurement of renal function is performed in all animals as described in Example 5.

Results and Comments

Five days after completion of Orellanine treatment the tumors in the treated animals have all stopped growing and turned bluish, while control tumors continue to grow. After two weeks the tumors of the control animals have approximately doubled in size, while the tumors in the animals treated with PEG-conjugated Orellanine have diminished substantially in size compared to the time of injection. The remaining tumor tissue is necrotic in contrast to control tumors that remain viable.

At the same time, and similar to Example 5, animals treated with PEG-conjugated Orellanine preserve 50-100% of their glomerular filtration rate (GFR) compared to the untreated controls.

This clearly demonstrates that PEG-conjugated Orellanine retains its tumor-killing activity in an in vivo-system, while simultaneously preserving renal function to a degree that would leave the patient with enough residual GFR to obviate the need for dialysis treatment.

Example 10

Effect of Astatine 211-Labeled Orellanine In-Vivo in a Rat Model of Renal Cell Carcinoma Background and Methodology Athymic, T cell-deficient rats (RNU, Charles River Laboratories, FRG) are used as a system for in vivo-growth of human renal cell carcinomas. The absence of a T cell-based immune defense in these animals makes them tolerant towards xenografts. One week after arrival in the animal facility 12 animals receive an X-irradiation dose of 5 Gy in order to suppress also their B cell-mediated response.

Three days later the animals are inoculated subcutaneously in the shoulder region with approximately $10 \times 10^6$ human renal carcinoma cells (SKRC-52). After several days, when localized tumors are palpable under the animals' skin, 6 animals are surgically equipped with an indwelling catheter for peritoneal dialysis (PD). (PD treatment will replace the renal function that is lost as a side effect upon administration of Orellanine.) After the surgical procedure each of these 6 animals receives 5 mg/kg of unlabeled Orellanine, mainly to shut down the kidneys and prevent excessive urinary loss of labeled Orellanine administered subsequently. The following day, dialysis is started via the PD-catheter, and two days post-op the animals receive 0.5 mg/kg $^{211}$At-labeled Orellanine, injected intravenously immediately after the last PD-cycle of the day. This procedure is repeated day 3 and day 4 post-op.

Results and Comments

Already at the end of treatment, day 4 post-op, it is evident by visual inspection that the tumors are turning necrotic (bluish appearance through the skin), and during the following few days they shrink substantially. When terminating the experiment 10 days after completion of the treatment (14 days post-op), the tumors have shrunk to approximately 10% of the mass before treatment, and the remaining tissue is necrotic.

These results, achieved with a much lower dose of Orellanine, clearly demonstrate the extra potency of $^{211}$At-labeled Orellanine compared to the unlabeled substance.

Example 11

Effect of PEG-Conjugated and Astatine 211-Labeled Orellanine In-Vivo in a Rat Model of Renal Cell Carcinoma Background and Methodology Athymic, T cell-deficient rats (RNU, Charles River Laboratories, FRG) are used as a system for in vivo-growth of human renal cell carcinomas. The absence of a T cell-based immune defense in these animals makes them tolerant towards xenografts. One week after arrival in the animal facility 12 animals receive an X-irradiation dose of 5 Gy in order to suppress also their B cell-mediated response.

Three days later the animals are inoculated subcutaneously in the shoulder region with approximately $10 \times 10^6$ human renal carcinoma cells (SKRC-52). After several days, when localized tumors are palpable under the animals' skin, 6 animals are surgically equipped with an indwelling catheter for peritoneal dialysis (PD). (PD treatment will replace the renal function that is lost as a side effect upon administration of Orellanine.) After the surgical procedure each of these 6 animals receives an intravenously administered dose of PEG-conjugated, $^{211}$At-labeled Orellanine corresponding to 0.5 mg/kg unconjugated Orellanine. The following day, dialysis is started via the PD-catheter, and another dose of PEG-conjugated, $^{211}$At-labeled Orellanine, corresponding to 0.5 mg/kg unconjugated Orellanine, is injected intravenously immediately after the last PD-cycle of the day. This procedure is repeated a third time the following day.

The subcutaneous tumors are visually inspected through the skin daily. Two weeks after surgery the experiment is terminated and the tumors are excised. At the same occasion measurement of renal function is performed in all animals as described in Example 5.

Results and Comments

Already during the second day of treatment it is evident by visual inspection that the tumors are starting to turn necrotic (bluish appearance through the skin). They stop growing and during the following days they shrink substantially. When terminating the experiment after 14 days post-op the tumors have shrunk to approximately 10% of the mass before treatment, and the remaining tissue is necrotic. The GFR-measurements according to Example 5 show that animals treated with PEG-conjugated, $^{211}$At-labeled Orellanine preserve 50-100% of their glomerular filtration rate (GFR) compared to the controls.

These results, achieved with a much lower dose of Orellanine, clearly demonstrate the extra potency of PEG-conjugated, $^{211}$At-labeled Orellanine compared to the unlabeled substance. Simultaneously, renal function is preserved to a degree that would leave a human patient enough residual GFR to obviate the need for dialysis treatment.

Example 12

Effect of PEG-Conjugated Orellanine in a Human Patient Suffering from Advanced Renal Cell Carcinoma with Distant Metastases A patient in need of treatment for unilateral renal carcinoma with distant metastases is given a series of 10 intravenous injections of PEG-conjugated Orellanine in a regimen of one injection every second day for 20 days. The initial tumor burden of the patient is determined to be approximately 1 kg. Based on this value, the appropriate daily dose is determined to correspond to 140 mg unconjugated Orellanine (i.e., 2 mg/kg at b.w. 70 kg). This procedure, with repeated administration of smaller amounts of Orellanine, has the benefit of effecting a gradual buildup of Orellanine to lethal levels in the tumor tissue, which actively takes up the substance, while extracellular concentrations of the toxin are kept below levels that might cause side-effects. The progress of the disease is monitored for one month; where after additional serial administrations of PEG-conjugated Orellanine are given as needed to reduce the tumor mass further.

During the treatment, the mass of tumor tissue in the patient is decreasing, and at the conclusion of the treatment the renal cancer is completely eradicated, demonstrating the efficacy of PEG-conjugated Orellanine against renal clear cell carcinoma. Conjugation of Orellanine to PEG has reduced renal filtering of the substance and thereby largely prevented contact with, and uptake into, normal proximal tubular cells. This means that the patient has been able to preserve enough renal function to remain independent of hemodialysis/peritoneal dialysis therapy after successful treatment of his/her cancer.

Example 13

Effect of Astatine 211-Labeled Orellanine in a Human Patient Suffering from Advanced Renal Cell Carcinoma with Distant Metastases A patient in need of treatment for a renal carcinoma renal carcinoma with distant metastases is given a series of 10 daily intravenous injections of Orellanine. The initial tumor burden of the patient is determined to be approximately 1 kg. Based on this value, the appropriate daily dose is determined to 14 mg (0.2 mg/kg at b.w. 70 kg). Before the first injection, the patient is prepared for hemodialysis or peritoneal dialysis since the Orellanine treatment may destroy healthy renal epithelial tissue along with the killing of the cancer cells, thus leaving the patient with impaired renal function. Five hours after each injection, hemodialysis is started and maintained for 2 hours. This procedure, with repeated administration of smaller amounts of Orellanine, has the benefit of effecting a gradual buildup of Orellanine to lethal levels in the tumor tissue, which actively takes up the substance, while extracellular concentrations of the toxin are kept below levels that might cause side-effects. Optionally, if the disease is unilateral, the unaffected kidney may be surgically removed and cold-preserved during the treatment, and reimplantation attempted after conclusion of the treatment. The progress of the patient is monitored throughout and after the treatment, and additional serial administrations of Orellanine are given as needed to further suppress the renal carcinoma.

During the treatment, the mass of tumor tissue in the patient is decreasing rapidly, and at the conclusion of the treatment the renal cancer is completely eradicated, demonstrating the efficacy of a much smaller dose of the $^{211}$At-labeled Orellanine, compared to the unlabeled substance, against renal clear cell carcinoma. The patient is in stable remission and remains on dialysis treatment (hemo/PD) while waiting for a renal transplant.

Example 14

Effect of PEG-Conjugated and Astatine 211-Labeled Orellanine in a Human Patient Suffering from Advanced Renal Cell Carcinoma with Distant Metastases A patient in need of treatment for unilateral renal carcinoma with distant metastases is given a series of 10 intravenous injections of PEG-conjugated and $^{211}$At-labeled Orellanine in a regimen of one injection every second day for 20 days. The initial tumor burden of the patient is determined to be approximately 1 kg. Based on this value, the appropriate daily dose is determined to correspond to 14 mg unconjugated Orellanine (0.2 mg/kg at b.w. 70 kg). This procedure, with repeated administration of smaller amounts of Orellanine, has the benefit of effecting a gradual buildup of Orellanine to lethal levels in the tumor tissue, which actively takes up the substance, while extracellular concentrations of the toxin are kept below levels that might cause side-effects. The progress of the disease is monitored for one month, where after additional serial administrations of PEG-conjugated and $^{211}$At-labeled Orellanine are given as needed to reduce the tumor mass further.

During the treatment, the mass of tumor tissue in the patient is decreasing rapidly, and at the conclusion of the treatment the renal cancer is completely eradicated, demonstrating the efficacy of a much smaller dose of the $^{211}$At-labeled Orellanine, compared to the unlabeled substance, against renal clear cell carcinoma. Conjugation of $^{211}$At-labeled Orellanine to PEG has reduced renal filtering of the substance and thereby largely prevented contact with, and uptake into, normal proximal tubular cells. This means that the patient has been able to preserve enough renal function to remain independent of hemodialysis/peritoneal dialysis therapy after successful treatment of his/her cancer.

The invention claimed is:

1. A method for treating a patient in need thereof against renal cell carcinoma, said method comprising administering to the patient a conjugate comprising a compound according to the Formula I:

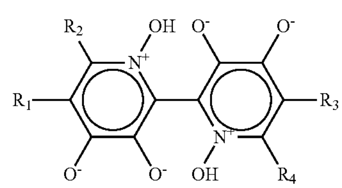

and a compound selected from the group consisting of:

a) at least one macromolecule of sufficient molecular weight and molecular diameter to substantially or completely prevent passage of the conjugate through the glomerular filter of the kidneys and entering primary urine, wherein the at least one macromolecule is covalently bound to the compound of Formula 1, and/or b) at least one cytotoxic agent;

wherein

R1, R2, R3 and/or R4 in Formula I, are selected from the group consisting of: hydrogen, amino, mercapto, carboxy, phosphate and halo, including fluoro, chloro, and bromo, C1-C6 alkyl, C1-C6 alkenyl, C1-C6 alkynyl, C1-C6 alkanol, C1-C6 alkenol, C1-C6 alkoxy, and C1-C6 alkenoxy, and wherein each of which, C1-C6 alkyl, C1-C6 alkenyl, C1-C6 alkynyl, C1-C6 alkanol, C1-C6 alkenol, C1-C6 alkoxy, and C1-C6 alkenoxy may be further substituted with moieties selected from the group consisting of amino, mercapto, carboxy, phosphate and halo, including fluoro, chloro, and bromo, or a pharmaceutically acceptable salt thereof.

2. The method of claim 1, wherein the conjugate comprising the compound of Formula I bound to a macromolecule and/or a cytotoxic agent is a pharmaceutically acceptable salt.

3. The method of claim 1, wherein the at least one macromolecule is selected from the group consisting of a polypeptide, a polyethylene glycol, a dextran and a Ficoll.

4. The method of claim 1, wherein the at least one cytotoxic agent is selected from the group consisting of a toxin and a radionuclide.

5. The method of claim 4, wherein the radionuclide is chosen from the group consisting of Astatine-211, Bismuth-212, Bismuth-213, Actinium-225, Lead-212 and Terbium-149.

6. The method of claim 4, wherein the radionuclide is Astatine-211.

7. The method of claim 1, wherein the conjugate is administered in sequential doses between two and seven days apart.

8. The method of claim 1, wherein the compound is administered daily.

9. The method of claim 1, wherein the compound is administered by at least one mode selected from parenteral, subcutaneous, intramuscular, intravenous, intrarticular, intrabronchial, intraabdominal, intracapsular, intracartilaginous, intracavitary, intracelial, intracerebellar, intracerebroventricular, intracolic, intracervical, intragastric, intrahepatic, intramyocardial, intraosteal, intrapelvic, intrapericardic, intraperitoneal, intrapleural, intraprostatic, intrapulmonary, intrarectal, intrarenal, intraretinal, intraspinal, intrasynovial, intrathoracic, intrauterine, intravesical, intralesional, bolus, vaginal, rectal, buccal, sublingual, intranasal, or transdermal.

10. A conjugate comprising a compound according to Formula I:

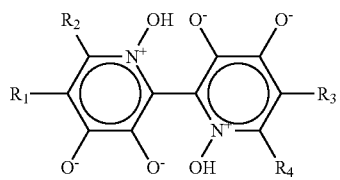

and a compound selected from the group consisting of:
a) at least one macromolecule of sufficient molecular weight and molecular diameter to substantially or completely prevent passage of the conjugate through the glomerular filter of the kidneys and entering primary urine, wherein the at least one macromolecule is covalently bound to the compound of Formula 1,
and/or
b) at least one cytotoxic agent;
wherein
R1, R2, R3 and/or R4 in Formula I, are selected from the group consisting of: hydrogen, amino, mercapto, carboxy, phosphate and halo, including fluoro, chloro, and bromo, C1-C6 alkyl, C1-C6 alkenyl, C1-C6 alkynyl, C1-C6 alkanol, C1-C6 alkenol, C1-C6 alkoxy, and C1-C6 alkenoxy, and wherein each of which, C1-C6 alkyl, C1-C6 alkenyl, C1-C6 alkynyl, C1-C6 alkanol, C1-C6 alkenol, C1-C6 alkoxy, and C1-C6 alkenoxy may be further substituted with moieties selected from the group consisting of amino, mercapto, carboxy, phosphate and halo, including fluoro, chloro, and bromo or the equivalent molar amount of a pharmaceutically acceptable salt thereof, for use as a medicament in the treatment of renal cell carcinoma.

11. A pharmaceutical composition comprising the compound according to claim 10, wherein the at least one macromolecule is selected from the group consisting of a polypeptide, a polyethylene glycol, a dextran and a Ficoll.

12. The pharmaceutical composition of claim 11, wherein the compound is a pharmaceutically acceptable salt.

13. The pharmaceutical composition of claim 11, wherein the composition is formulated for parenteral, subcutaneous, intramuscular, intravenous, intrarticular, intrabronchial, intraabdominal, intracapsular, intracartilaginous, intracavitary, intracelial, intracerebellar, intracerebroventricular, intracolic, intracervical, intragastric, intrahepatic, intramyocardial, intraosteal, intrapelvic, intrapericardic, intraperitoneal, intrapleural, intraprostatic, intrapulmonary, intrarectal, intrarenal, intraretinal, intraspinal, intrasynovial, intrathoracic, intrauterine, intravesical, intralesional, bolus, vaginal, rectal, buccal, sublingual, intranasal, or transdermal administration to a patient.

14. A pharmaceutical composition comprising the compound according to claim 10, wherein the at least one cytotoxic agent is selected from the group consisting of a toxin and a radionuclide.

15. The pharmaceutical composition of claim 14, wherein the compound is a pharmaceutically acceptable salt.

16. The method of claim 14, wherein the radionuclide is Astatine-211.

* * * * *